(12) United States Patent
Shen et al.

(10) Patent No.: US 10,932,852 B2
(45) Date of Patent: Mar. 2, 2021

(54) ELECTROPHYSIOLOGY CATHETER

(71) Applicant: SHANGHAI MICROPORT EP MEDTECH CO., LTD., Shanghai (CN)

(72) Inventors: Lei Shen, Shanghai (CN); Hui Wang, Shanghai (CN); Tao Miao, Shanghai (CN); Bo Liang, Shanghai (CN); Jiahong Tan, Shanghai (CN)

(73) Assignee: SHANGHAI MICROPORT EP MEDTECH CO., LTD., Shanghai (CN)

( * ) Notice: Subject to any disclaimer, the term of this patent is extended or adjusted under 35 U.S.C. 154(b) by 75 days.

(21) Appl. No.: 16/321,607

(22) PCT Filed: Jun. 28, 2017

(86) PCT No.: PCT/CN2017/090617
§ 371 (c)(1),
(2) Date: Jan. 29, 2019

(87) PCT Pub. No.: WO2018/019077
PCT Pub. Date: Feb. 1, 2018

(65) Prior Publication Data
US 2019/0307504 A1    Oct. 10, 2019

(30) Foreign Application Priority Data
Jul. 29, 2016  (CN) .......................... 201610608765.2
Aug. 10, 2016  (CN) .......................... 201610651602.2

(51) Int. Cl.
*A61B 18/14*    (2006.01)
*A61B 5/042*    (2006.01)
(Continued)

(52) U.S. Cl.
CPC ........ *A61B 18/1492* (2013.01); *A61B 5/0422* (2013.01); *G01L 1/2262* (2013.01);
(Continued)

(58) Field of Classification Search
CPC . A61B 18/1492; A61B 5/0422; A61B 5/6852; A61B 2018/00577;
(Continued)

(56) References Cited

U.S. PATENT DOCUMENTS

| 8,621,939 B2* | 1/2014 | Blumenkranz | A61B 34/37 |
| | | | 73/862.046 |
| 10,067,009 B2* | 9/2018 | Jaeger | G01L 1/2218 |
| 2020/0100859 A1* | 4/2020 | Shen | A61B 18/1492 |

FOREIGN PATENT DOCUMENTS

| CN | 85104807 B | 8/1986 |
| CN | 2190296 Y | 2/1995 |

(Continued)

*Primary Examiner* — Octavia Hollington
(74) *Attorney, Agent, or Firm* — Muncy, Geissler, Olds & Lowe, P.C.

(57) ABSTRACT

An electrophysiology catheter (100) includes a catheter distal portion (110) on which a force sensor (200) is arranged. The force sensor (200) includes an elastic tube (210) and strain gauges (220). The elastic tube (210) has a hollow portion in its wall, and the strain gauges (220) are disposed external to the hollow portion. Compared to the design with the strain gauges (220) overlapping the hollow portion, arranging them over solid portions of the elastic tube (210) allows the strain gauges (220) to collect more accurate electrical signals while suffering from less interference. This can result in a significant improvement in contact force measurement accuracy of the catheter distal portion (110).

19 Claims, 7 Drawing Sheets

(51) Int. Cl.
*G01L 1/22* (2006.01)
*A61B 5/00* (2006.01)
*A61B 18/00* (2006.01)
*A61M 25/01* (2006.01)
*A61M 25/00* (2006.01)
*G01B 5/30* (2006.01)

(52) U.S. Cl.
CPC .......... *G01L 1/2287* (2013.01); *A61B 5/6852* (2013.01); *A61B 5/6885* (2013.01); *A61B 2018/00577* (2013.01); *A61B 2018/00773* (2013.01); *A61B 2018/1435* (2013.01); *A61B 2562/0266* (2013.01); *A61M 25/0141* (2013.01); *A61M 2025/0002* (2013.01); *G01B 5/30* (2013.01)

(58) Field of Classification Search
CPC ........ A61B 2018/00773; A61B 5/6885; A61B 2018/1435; A61B 2562/0266; G01L 1/2262; G01L 1/2887; G01B 7/18; G01B 5/30; A61M 25/0141; A61M 2025/0002
USPC ..................................................... 73/862.635
See application file for complete search history.

(56) References Cited

FOREIGN PATENT DOCUMENTS

| | | | |
|---|---|---|---|
| CN | 1148166 | A | 4/1997 |
| CN | 2296528 | Y | 11/1998 |
| CN | 1229915 | A | 9/1999 |
| CN | 2463813 | Y | 12/2001 |
| CN | 101034022 | A | 9/2007 |
| CN | 201108496 | Y | 9/2008 |
| CN | 202255731 | U | 5/2012 |
| CN | 202676329 | U | 1/2013 |
| CN | 202735022 | U | 2/2013 |
| CN | 103349558 | A | 10/2013 |
| CN | 103750898 | * | 4/2014 |
| CN | 103750898 | A | 4/2014 |
| CN | 103800017 | A | 5/2014 |
| CN | 204072317 | U | 1/2015 |
| CN | 104367324 | A | 2/2015 |
| CN | 204318750 | U | 5/2015 |
| CN | 105012009 | A | 11/2015 |
| CN | 105120939 | * | 12/2015 |
| CN | 105120939 | A | 12/2015 |
| CN | 105167839 | A | 12/2015 |
| CN | 105434035 | A | 3/2016 |
| CN | 205234628 | * | 5/2016 |
| CN | 205234628 | U | 5/2016 |
| CN | 105615990 | A | 6/2016 |
| CN | 105686819 | A | 6/2016 |
| CN | 106264719 | A | 1/2017 |
| EP | 2172240 | A1 | 4/2010 |
| EP | 2338430 | A1 | 6/2011 |
| EP | 2626680 | A1 | 8/2013 |
| WO | WO2009/007857 | A2 | 1/2009 |
| WO | WO 2012142588 | A1 | 10/2012 |
| WO | WO 2013071361 | A1 | 5/2013 |

* cited by examiner

ELECTROPHYSIOLOGY CATHETER

TECHNICAL FIELD

The present invention relates to the field of medical devices and, in particular, to an electrophysiology catheter.

BACKGROUND

In recent years, catheter systems have been developed for interventional treatment of, for example, cardiac arrhythmias and refractory hypertension. For example, in the treatment of atrial fibrillation, one type of cardiac arrhythmia, an ablation or mapping catheter may be introduced into the heart via a vein or artery to find an aberrant electrical signal trigger or pathway by endocardial mapping, and then apply energy to the trigger or pathway to ablate it to eliminate or alter undesirable electrical signals, thus achieving curative results. Another example is the treatment of refractory hypertension through renal artery ablation, in which an ablation catheter may be arterially introduced into an artery connecting the abdominal aorta and the kidney to ablate and block the parasympathetic nerve pathway to lower the blood pressure.

For ablation therapy, how strongly an electrode disposed on a distal end of the used catheter contacts the target vessel wall or tissue is considered very important. Weak contact will lead to a shallow lesion incapable of allowing effective blockage of the aberrant electrical signals or nerve conduction. However, excessively strong contact may probably lead to perforation of the tissue, which causes an increased safety risk. In order to avoid these issues, existing catheters of this type are all provided at the distal end with force sensors to effectively measure the contact force between the electrode and the vessel wall or tissue. For instance, magnetic position sensors may be equipped in such a catheter to sense contact strength between the distal end thereof and the target organ. However, such sensors suffer from certain limitations in practical use, such as tending to give distorted results due to interference from external magnetic fields and limiting other catheter functionalities such as three-dimensional magnetic positioning due to the use of magnetic fields. There are also catheter systems using force-sensitive materials as force sensors for sensing loads on the distal end. Although such systems are good at axial load measurement, they are lack of accuracy in non-axial load measurement. There are still other catheters employing fiber-optic systems for sensing contact forces with the vessel wall or organ, but they are difficult to package and make and expensive and require external electrical signal devices.

In view of the above-described limitations in practical application of all the conventional systems, it is necessary to develop a force sensing device that is capable of measuring contact strength at the distal end and suitable for mass production.

SUMMARY OF THE INVENTION

It is an objective of the present invention to address the inability of conventional systems to accurately measure contact forces at a distal catheter end by presenting an electrophysiology catheter.

In order to achieve the above and other related objects, the present invention provides an electrophysiology catheter including a catheter distal portion, wherein the catheter distal portion is provided with a force sensor, the force sensor including an elastic tube and a strain gauge, the elastic tube having a hollow portion formed in a wall thereof, the strain gauge disposed external to the hollow portion.

Preferably, the hollow portion may include at least one arcuate first through-slot, each first through-slot having opposing ends between which one strain gauge is arranged or a plurality of strain gauges are arranged side-by-side.

Preferably, the hollow portion may include a plurality of first through-slots axially spaced apart from one another on the elastic tube and staggered from one another along a circumferential direction of the elastic tube.

Preferably, the hollow portion may include two first through-slots, wherein one strain gauge is disposed between opposing ends of one of the first through-slots, while two strain gauges are disposed side-by-side between opposing ends of the other one of the first through-slots, and wherein one of the first through-slots has a length greater than a length of the other one of the first through-slots.

Preferably, the hollow portion may include more than two first through-slots distributed evenly along the circumferential direction of the elastic tube, each first through-slot having two opposing ends between which one strain gauge is disposed.

Preferably, a central axis of the strain gauge along an axial direction of the elastic tube may be parallel to a central axis of the elastic tube.

Preferably, the hollow portion may include at least one through-slot set, each through-slot set containing a plurality of first through-slots aligned with one another axially and having two opposing ends between which one strain gauge is arranged or a plurality of strain gauges are arranged side-by-side.

Preferably, a length of the strain gauge in an axial direction of the elastic tube may be greater than or equal to a width of the through-slot set in the axial direction of the elastic tube.

Preferably, the hollow portion may include a plurality of through-slot sets axially spaced apart from one another on the elastic tube and staggered from one another along a circumferential direction of the elastic tube.

Preferably, the hollow portion may include two through-slot sets, wherein one strain gauge is disposed between opposing ends of one of the through-slot sets, while two strain gauges are disposed side-by-side between opposing ends of the other one of the through-slot sets, and wherein one of the through-slot sets has a length greater than a length of the other one of the through-slot sets.

Preferably, the hollow portion may include more than two through-slot sets distributed evenly along the circumferential direction of the elastic tube, each through-slot set having two opposing ends between which one strain gauge is disposed.

Preferably, a central axis of the strain gauge along an axial direction of the elastic tube may be parallel to a central axis of the elastic tube.

Preferably, each of the first through-slots may be provided at opposing ends thereof with second through-slots extending along an axial direction of the elastic tube.

Preferably, the second through-slots may have an obround, oval or round shape.

Preferably, the hollow portion may include at least one spiral third through-slot, wherein the strain gauge extends in a same direction as the spiral third through-slot.

Preferably, the hollow portion may include a plurality of third through-slots spaced apart from one another, one or more strain gauges are disposed between every adjacent two of the plurality of third through-slots.

Preferably, the strain gauges may be disposed in central portions of the third through-slots.

Preferably, the third through-slot may be formed by spiral cutting at a pitch of 1.0-6.0 mm and a number of turns of 1-3, the third through-slot having a width of 0.05-0.2 mm.

Preferably, the hollow portion may include a plurality of fourth through-slots extending in an axial direction of the elastic tube and spaced apart from one another along a circumferential direction of the elastic tube, wherein one or more strain gauges are disposed side-by-side between every adjacent two of the plurality of fourth through-slots.

Preferably, the elastic tube may be provided with sleeves at opposing ends thereof and resumes an "I"-shaped structure.

In summary, compared to the design with the strain sensors overlapping the hollow portion, arranging them over solid portions of the elastic tube in the electrophysiology catheter of the present invention allows the strain gauges to collect more accurate electrical signals and thus improve contact force measurement accuracy of the catheter distal portion.

In particular, disposing the strain gauges between opposing ends of the arcuate first through-slots or between adjacent spiral third through-slots or between adjacent axially-extending fourth through-slots in accordance with the present invention enables the strain gauges to collect higher-quality electrical signals. Moreover, the spiral third through-slots impart higher circumferential uniformity to the elastic tube, helping in collecting more accurate electrical signals.

In more particular, the axially-extending second through-slots provided at the ends of the first through-slots in accordance with the present invention can further lower the rigidity of the elastic tube, thereby increasing the deformability of the elastic tube, helping in enhancing the electrical signals collected by the strain gauges and making the measurement results more accurate.

Further, the force sensor according to the present invention is less bulky, more sensitive, less affected by magnetic fields, immune from temperature variations and cost-effective. Furthermore, in addition to the magnitude of a contact force exerted by the surface of a vessel wall or organ on the catheter distal portion, the plurality of strain gauges can also measure axial and lateral components of the force and an associated contact angle as well. This can provide the physician with valuable additional information based on which better surgical outcomes can be obtained.

In these figures,

100—ablation catheter; 110—catheter distal portion; 120—deflectable section; 130—main body; 140—control handle; 150—ablation electrode; 160—signal conditioning circuit board; 170—trailing wire; 180—data acquisition device; 190—microprocessor; 200—force sensor; 210, 310, 410, 510—elastic tubes; 220, 430—strain gauges; 230—through-slot set; 231—first through-slot; 240—second through-slot; 420—third through-slot; 511—tubular body; 520—sleeve; 530—fourth through-slot; 20—percutaneous sheath; 30—left atrium; 40—distal outer tube.

DETAILED DESCRIPTION

The present invention will be described in greater detail with reference to FIGS. 1 to 14 so that the invention will become more apparent and readily understood. Of course, the present invention is not limited to the following specific embodiments, and general substitutions well known to those skilled in the art are also embraced within the scope thereof.

Additionally, while the present invention is described in detail with reference to the annexed schematic figures, these figures are presented only for the purpose of facilitating the detailed description of the embodiments rather than limiting the invention in any sense.

As used herein, the terms "proximal" and "distal" describe relative orientations, relative positions and directions between elements or actions, viewed by a physician operating the product. Without wishing to be limiting, a "proximal end" usually refers to an end of the product close to the physician during normal operation, while a "distal end" usually refers to an end thereof that enters the patient first. "Axial" and "circumferential" refer to directions along the axis and circumference of an elastic tube.

As used in the specification, and in the appended claims, the singular forms "a," "an," "the" include plural referents unless the context clearly dictates otherwise. As used in the specification, and in the appended claims, the term "or" is employed in the sense including "and/or" unless the context clearly dictates otherwise.

Embodiment 1

Figure 1:
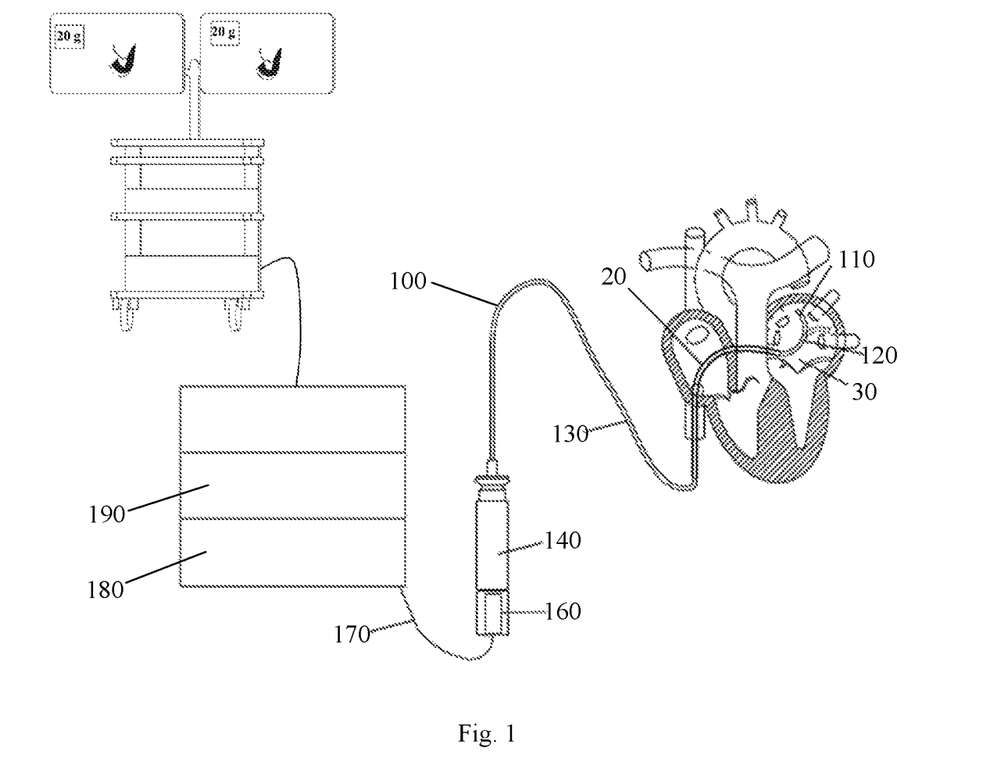
FIG. 1 is a schematic illustrating cardiac ablation carried out by an ablation catheter according to Embodiment 1 of the present invention.
Figure 2:
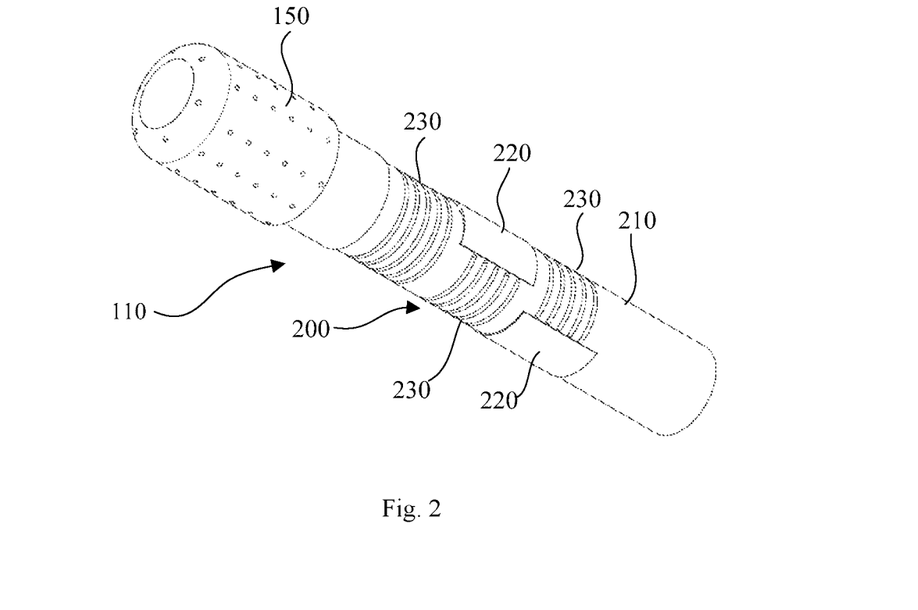
FIG. 2 is a structural schematic of a distal portion of the ablation catheter according to Embodiment 1 of the present invention.

FIG. 1 is a schematic illustrating cardiac ablation carried out with an ablation catheter according to Embodiment 1 of the present invention. FIG. 2 is a structural schematic of a distal portion of the ablation catheter according to Embodiment 1 of the present invention.

Referring to FIGS. 1 and 2, the ablation catheter 100 include, sequentially connected, the catheter distal portion 110, a deflectable section 120, a main body 130 and a control handle 140. The catheter distal portion 110 is equipped with an ablation electrode 150 intended to be brought into contact with a vessel wall or tissue and apply energy thereto for ablation. However, the catheter distal portion 110 is not limited to be equipped with the ablation electrode 150, since a mapping electrode may be alternatively equipped thereon. In application, the ablation catheter 100 will be inserted through a percutaneous sheath 20 and the inferior vena cava into the left atrium 30 to perform ablation there.

For the sake of brevity, it is assumed hereinafter that the catheter distal portion 110 is equipped with the ablation electrode 150. However, those skilled in the art may modify details in the following description so that it is applicable to an electrode of a different type. When the catheter distal portion 110 exerts a force on the vessel wall or tissue, a reaction force will be generated by the vessel wall or tissue on the catheter distal portion 110 and will be measured in accordance with the present invention as a contact force.

In this Embodiment, the ablation electrode 150 is fabricated from a metal material such as a stainless steel or a platinum-iridium alloy. The ablation electrode 150 has a porous structure. In other embodiments, it may also be free of pores. The control handle 140 can control the deflectable section 120 and cause deflection thereof. The main body of the ablation catheter 100 is generally a polymer tube, such as a polyurethane (PU), PEBAX (nylon elastomer) or nylon tube, or a PU tube with a woven metal mesh, having a diameter not exceeding 9F. The control handle 140 is provided therein with a signal conditioning circuit board 160 for amplifying and filtering received electrical signals. The ablation catheter 100 is connected to data acquisition devices 180 and a microprocessor 190 in a backend control system via trailing wires 170. The data acquisition devices 180 are configured to collect the amplified and filtered electrical signals from the signal conditioning circuit board 160 and relay them to the microprocessor 190 which processes the signals and output contact force data and contact angle data. The microprocessor 190 contains related programs or algorithms for computationally processing the amplified and filtered electrical signals and obtaining the contact force data and contact angle data.

In the case shown in FIG. 2, the catheter distal portion 110 is further provided with a force sensor 200. The force sensor 200 is capable of sensing the magnitude and orientation of the contact force created from the contact of the ablation electrode 150 on the catheter distal portion 110 with the surface of the vessel wall or tissue. When the catheter distal portion 110 is subjected to the contact force, the electrical signals from the force sensor 200 will experience changes, and the changed electrical signals will be received, amplified and filtered, and provided to the data acquisition devices 180 by the signal conditioning circuit board 160.

In this Embodiment, the force sensor 200 is attached to the ablation electrode 150, and this attachment may be accomplished by bonding using an epoxy-based resin or another adhesive, or by laser welding or the like.

The force sensor 200 includes an elastic tube 210 and at least three strain gauges 220. The at least three strain gauges 220 are disposed on an outer surface of the elastic tube 210 and configured to sense strains in at least three directions.

Figure 3:
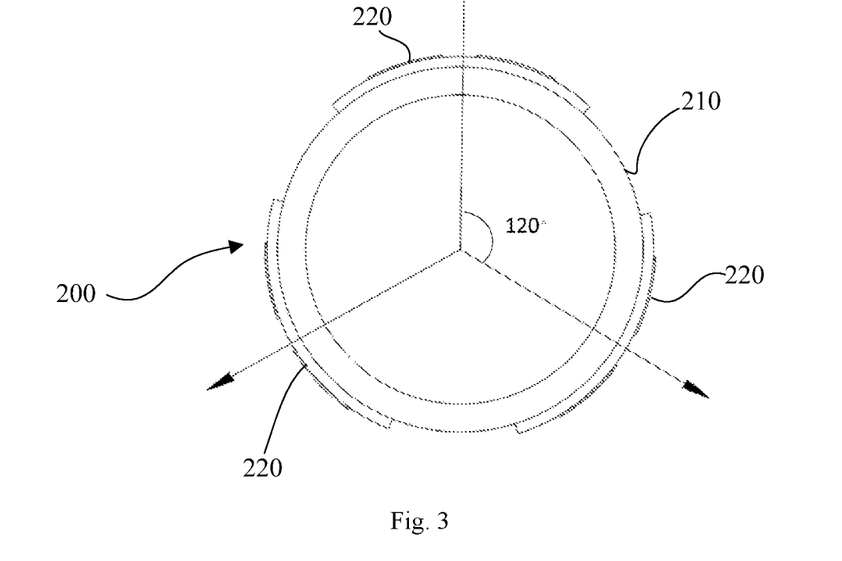
FIG. 3 schematically illustrates how strain gauges are distributed on an elastic tube according to Embodiment 1 of the present invention.

In Embodiment 1 of the present invention, the at least three strain gauges 220 are disposed over respective circumferential sections. That is, they are staggered from one another along the axial direction of the elastic tube 210. Moreover, the at least three strain gauges 220 are also staggered from one another along the circumferential direction of the elastic tube 210. That is, they are spaced apart and staggered from one another circumferentially. In this Embodiment, the number of the strain gauges 220 is preferred to be three. This makes it possible not only to satisfy the practical need for contact force measurement but to achieve cost control and prevent bulkiness of the catheter. Projections of the three strain gauges 220 on a plane crossing the axis of the elastic tube 210 at right angles are preferably distributed evenly along the circumference thereof. FIG. 3 schematically illustrates a distribution of the strain gauges on the elastic tube according to Embodiment 1 of the present invention. As shown in FIG. 3, when projected onto a plane orthogonal to the axis of the elastic tube, the three strain gauges 220 are circumferentially distributed evenly (i.e., their centers divide the circumference into three equal 120-degree arcs).

From the above description, those skilled in the art will appreciate that, as described herein, the even circumferential distribution of the strain gauges 220 with respect to the elastic tube 210 also includes the even circumferential distribution of the strain gauges 220's orthographic projections on a plane perpendicular to the axis of the elastic tube.

The following description will be made in the exemplary context of three strain gauges 220 in order to facilitate the explanation of the present invention. However, the present invention is not limited to such embodiments with three strain gauges 220, because more than three strain gauges 220 may also be included. In this case, their orthographic projections on a plane perpendicular to the axis of the elastic tube are similarly preferred to be distributed evenly along the circumference of the elastic tube 210.

With continued reference to FIG. 2, the elastic tube 210 is coupled at its distal end to the ablation electrode 150. The elastic tube 210 has a length of 5.0-10.0 mm, and a ratio of its diameter to that of the ablation catheter 100 ranges from 0.6 to 0.9. The elastic tube 210 is an elastic plastic or rubber (polymer) tube or a metal tube. Preferably, the metal tube is fabricated from a shape memory metal material such as a nickel titanium alloy or a stainless steel.

Each of the strain gauges 220 essentially consists of a strain-sensitive grid and a backing. The strain-sensitive grid is fabricated by etching a constantan or nichrome foil into a grid-like pattern and glued to the backing which is a semi-rigid polymer sheet. The polymer from which the semi-rigid backing is fabricated is polyimide (PI) or polyetheretherketone (PEEK), with PEEK being preferred. The backing has a thickness of from 5.0 μm to 10.0 μm.

The strain gauges 220 may either be common ones such as single- or half-bridge strain gauges or uncommon ones such as shear gauges or strain rosettes. There is no particular limitation on the type of the strain gauges, and a proper type can be selected essentially based on the structure of the elastic tube 210. The strain gauges 220 each have a resistance of 120Ω to 350Ω and a gauge factor of 2.2. In addition, in order for easier attachment to be achieved, each of them has a width that is smaller than or equal to 2.0 mm, preferably 0.5-2 mm, and a length that is smaller than or equal to 5.0 mm, preferably 1.0-5.0 mm. Preferably, the strain gauges 220 have good performance in terms of accuracy and sensitivity and are immune from temperature changes, in order to ensure good measurement results. The strain gauges 220 are fixed to the outer surface of the elastic tube 210. Preferably, they are fixed to the outer surface of the elastic tube 210 using an epoxy- or acrylic-based adhesive or using a hot melt adhesive or the like.

Preferably, in this Embodiment, the elastic tube 210 has a hollow portion in its outer surface (i.e., slots cut through the outer surface of the elastic tube 210) which imparts better elasticity to the elastic tube 210 (especially in the case of a metal tube) and increases the deformability thereof. As such, the strain gauges 220 can sense larger deformations and output electrical signals that have undergone associated changes. More preferably, in this Embodiment, the strain gauges 220 are disposed over portions of the outer surface of the elastic tube 210 other than the hollow portion (i.e., solid portions of the elastic tube 210, as more clearly seen in FIG. 2). In other words, the strain gauges 220 do not overlap the hollow portion at all. This, when compared with the arrangement with the strain gauges 220 overlapping the hollow portion, this arrangement can effectively avoid signal interference and thus collect more accurate electrical signals. As a result, the force sensor 200 of the present invention can collect higher-quality electrical signals from the strain gauges 220, which enable more accurate measurement of the contact force acting on the catheter distal portion 110.

Figure 4:
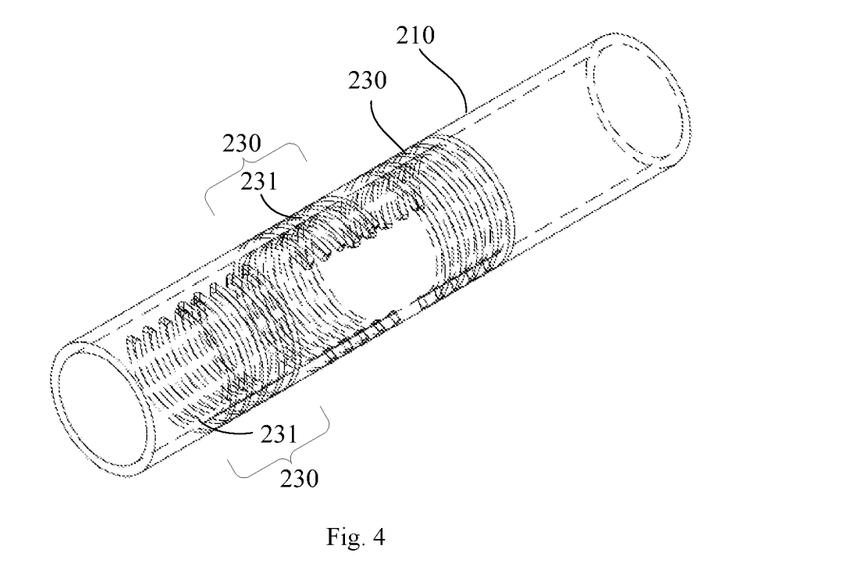
FIG. 4 is a structural schematic of the elastic tube with through-slot sets according to Embodiment 1 of the present invention.

FIG. 4 is a structural schematic of the elastic tube with through-slot sets according to Embodiment 1 of the present invention. As shown in the figure, in this Embodiment, the hollow portion includes the through-slot sets 230. Each of the through-slot sets 230 includes a plurality of first through-slots 231 arranged side-by-side axially. Each of the first through-slots 231 is an arcuate slot cut in the elastic tube 210 extending along the circumference thereof. Preferably, a length of each first through-slot 231 is equal to two-thirds to four-fifths of the circumference of the elastic tube 210. Moreover, one or more of the side-by-side arranged strain gauges 220 are disposed over a non-slotted portion of the elastic tube between the opposing ends of a corresponding one of the through-slot sets 230 (shown in detail in FIG. 2). In the following description, a width of each of the through-slot sets 230 is defined as a total width that the plurality of first through-slots 231 contained therein spans axially, while a length of each of the through-slot sets 230 is defined as a length that each of the first through-slots 231 extends circumferentially.

Preferably, each of the strain gauges 220 extends axially a width that is equal to or greater than the width of a corresponding one of the through-slot sets 230. For example, the two ends of the strain gauge 220 (along the axial direction) may be either aligned with the respective ends of the through-slot set 230 or protrude beyond the respective ends of the through-slot set 230 in the same direction. More preferably, axially with respect to the elastic tube 210, central axes of the strain gauges 220 are parallel to those of the first through-slots 231 and of the elastic tube 210.

Each of the through-slot sets 230 contains three to seven, preferably, five first through-slots 231. According to this Embodiment, the plurality of through-slot sets 230 are provided on the elastic tube 210. Each of the through-slot sets 230 contains a plurality of first through-slots 231, which imparts greater elasticity to the elastic tube 210 and significantly facilitates strain sensing by the strain gauges 220.

As shown in FIG. 4, there are more than one through-slot sets 230. The through-slot sets 230 are staggered from one another axially along the elastic tube 210 and staggered from one another circumferentially with respect to the elastic tube 210 (preferably, evenly along the circumference). In each of the through-slot sets 230, the first through-slots 231 are spaced apart by a distance of 0.1-0.4 mm and each have a width of 0.05-0.2 mm. Those skilled in the art will appreciate that, as described herein, the even circumferential distribution of the strain gauges 220 with respect to the elastic tube 210 also includes the even circumferential distribution of the strain gauges 220's orthographic projections on a plane perpendicular to the axis of the elastic tube 210.

In this Embodiment, the number of the through-slot sets 230 is three (as shown in FIGS. 2 and 4), and a single one of the strain gauges 220 is disposed between the two ends of a corresponding one of the through-slot sets 230.

In another embodiment (not shown), the number of the through-slot sets 230 is two. Additionally, one strain gauge 220 is arranged between the two ends of one of the through-slot sets 230, and two strain gauges 220 are disposed between the opposing ends of the other through-slot set 230 (preferably, side-by-side circumferentially, i.e., on the same circumferential section of the elastic tube). The three strain gauges 220 are evenly distributed circumferentially with respect to the elastic tube, with their centers trisecting the circumference into three equal 120-degree arcs. For example, the length of one of the through-slot sets 230 may be greater than that of the other through-slot set 230. In other embodiments, there may also be more than three through-slot sets 230. The present invention is not limited to any particular number of through-slot sets, and those skilled in the art can select a proper number of through-slot sets based on the practical need.

Embodiment 2

Figure 5:
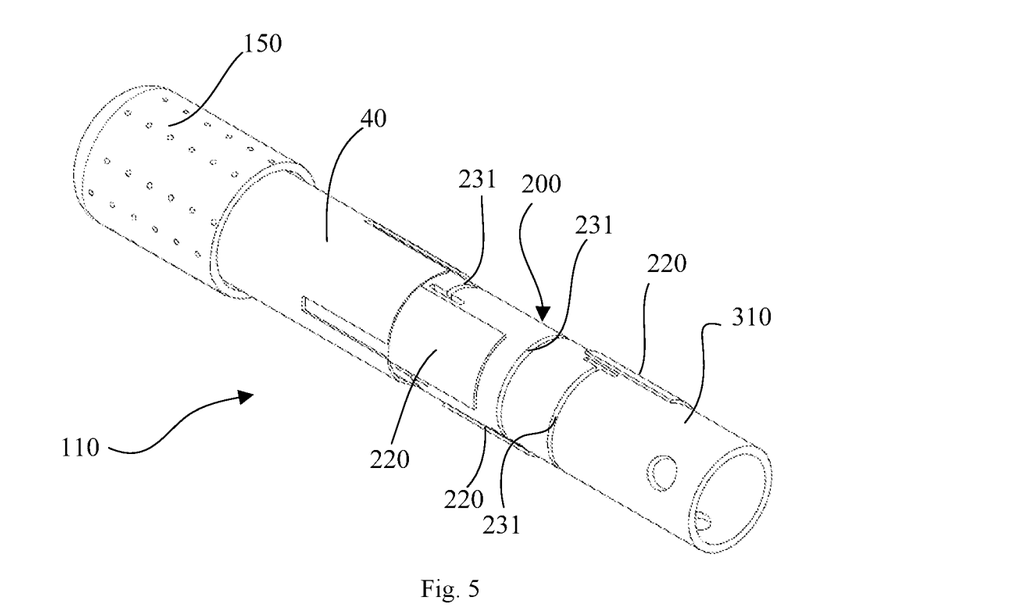
FIG. 5 is a structural schematic of a distal portion of an ablation catheter including an elastic tube with three arcuate through-slots according to Embodiment 2 of the present invention.
Figure 6:
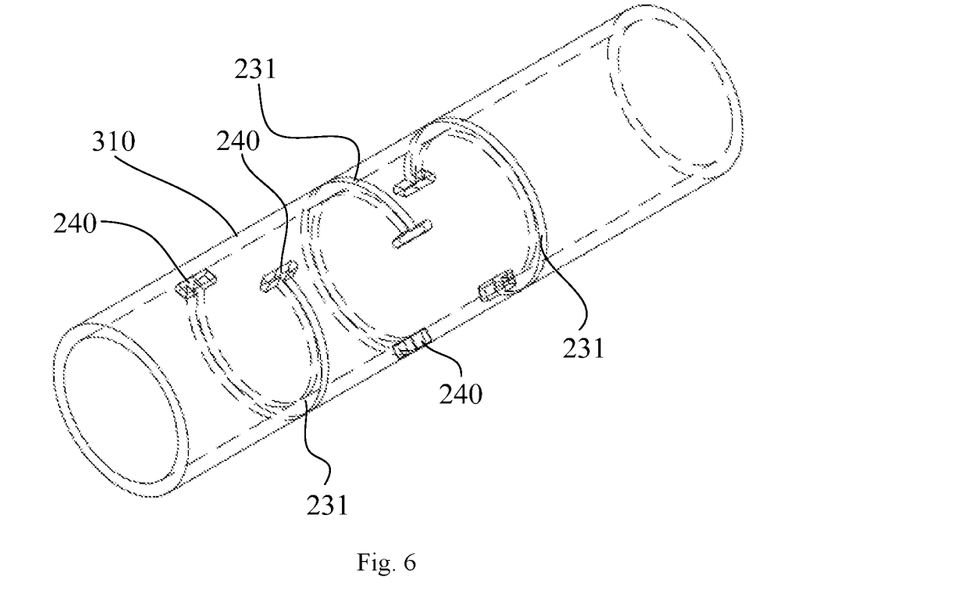
FIG. 6 is a structural schematic of the elastic tube according to Embodiment 2 of the present invention.

FIG. 5 shows a structural schematic of a distal portion of an ablation catheter according to Embodiment 2 of the present invention, and FIG. 6 is a structural schematic of an elastic tube according to Embodiment 2 of the invention. In the following description, a width of a first through-slot 231 is defined as a length that the first through-slot spans along the axial direction of the elastic tube, while a length of the first through-slot 231 is defined as a length the first through-slot 231 extends along the circumferential direction of the elastic tube.

In this Embodiment, the elastic tube 310 also has a hollow portion including arcuate first through-slots 231. Specifically, they may be arcuate slots cut in a single circumferential section of the outer surface of the elastic tube 310. Preferably, the length of each of the first through-slots 231 is two-thirds to four-fifths of the circumference of the elastic tube 310. The first through-slots 231 impart increased elasticity to the elastic tube 310 and allows for enhanced deformability thereof and collection of stronger electrical signals. In this Embodiment, each of the first through-slots 230 is an arcuate slot cut in the circumferential wall of the elastic tube. In other embodiments, the first through-slots 231 may also each be an arcuate slot of another type, such as a partially spiral slot. The present invention is not limited in this regard.

Differing from Embodiment 1, according to this Embodiment, the first through-slots 231 in the hollow portion are not grouped into through-slot set(s) 230 of the Embodiment 1, and the number of the first through-slots 231 is at least two. The at least two first through-slots 231 are spaced apart from one another along an axial direction of the elastic tube 310 and staggered from one another along the circumference of the elastic tube 310 (preferably, evenly in the circumferential direction). Moreover, the first through-slots 231 are spaced apart at a pitch of 1.0-2.0 mm (i.e., an axial spacing between adjacent through-slots) and have a width of 0.05-0.3 mm.

In one embodiment of the present invention, the number of the first through-slots 231 is same as that of the strain gauges 220. As shown in FIGS. 5 to 6, the number of the first through-slots 231 is three, and they are spaced apart from one another axially with respect to the elastic tube 310. Moreover, a single one of the strain gauges 220 is disposed over a non-slotted portion of the elastic tube between opposing ends of a corresponding one of the first through-slots 231. Preferably, the three strain gauges 221 are circumferentially distributed evenly, with their centers trisecting the circumference into three equal 120-degree arcs. More preferably, the three first through-slots 231 are also circumferentially distributed evenly, with their centers trisecting the circumference into three equal 120-degree arcs.

In a preferred embodiment, each of the strain gauges 220 is disposed equidistantly from the opposing ends of a corresponding one of the first through-slots 231. That is, a center of the strain gauge 220 is spaced from the opposing ends of the first through-slot 231 by equal distances.

In another embodiment of the present invention, the number of the first through-slots 231 is smaller than that of the strain gauges 220, which is not shown. Specifically, the number of the first through-slots 231 is two, and the two first through-slots 231 are similarly arranged side-by-side axially and staggered from each other circumferentially. Additionally, one strain gauge 220 is disposed between opposing ends of one of the first through-slots 231, and two strain gauges 220 are arranged between opposing ends of the other first through-slot 231. Similarly, the three strain gauges 220 are circumferentially distributed evenly, with their centers trisecting the circumference into three equal 120-degree arcs. In this case, the length of one of the first through-slots 231 may be optionally greater than that of the other first through-slot 231 so that there will be enough room for accommodating the two strain gauges 220 between the opposing ends of the shorter first through-slot 231. For example, the length of one of the first through-slots 231 is greater than or equal to two-thirds of the circumference of the elastic tube 310, while the length of the other first through-slot 231 is smaller than two-thirds of the circumference of the elastic tube 310.

In Embodiment 2, the strain gauges 220 are preferably arranged over the same circumferential section as the first through-slots 231, in order for better strain sensing to be achieved.

With continued reference to FIG. 6, second through-slots 240 may be formed at the opposing ends of each of the first through-slots 231. The second through-slots 240 may be obround, oval or round. As shown in FIG. 6, the second through-slots are preferred to be oblong, because this shape allows space savings, thus helping in miniaturization of the ablation catheter 100. Specifically, in case of oblong second through-slots 240, their longer sides extend axially. In case of oval second through-slots 240, their major axes extend axially. In the arrangement with the first through-slots 231 in the circumferential section of the elastic tube terminated at their circumferential ends at the second through-slots 240, preferably, along the axial direction of the elastic tube 310, central axes of the strain gauges 220 are parallel to those of the first through-slots 231 and of the elastic tube 310. With the second through-slots 240, it is possible to effectively prevent stress concentration at the ends of the first through-slots 231. In other embodiments, in place of the second through-slots 240 at the ends of the first through-slots 231, the first through-slots 231 may be curved at their ends or be partially spiral, without limitation. In a preferred embodiment, the strain gauges 220 are arranged close to the second through-slots 240 in order for better strain sensing to be achieved.

Figure 7:
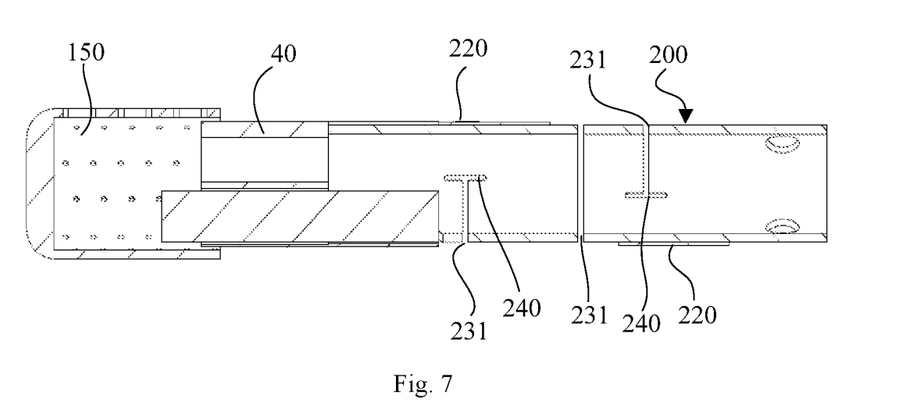
FIG. 7 is a schematic cross-sectional view of the distal portion of the ablation catheter according to Embodiment 2 of the present invention.

FIG. 7 is a schematic cross-sectional view of the distal portion of the ablation catheter according to Embodiment 2 of the present invention. As shown in FIG. 7 (in conjunction with FIG. 5), the distal portion of the elastic tube 310 is received within a distal outer tube 40. The distal outer tube 40 is a single-lumen tube flexible enough not to affect transmission of contact forces there. To this end, it may be made of PU, silicone rubber or another flexible material. The elastic tube 310 is a hollow tube with an inner diameter that is great enough to allow the passage of a component such as a saline perfusion tube, a magnetic positioner or an electrode lead therethrough.

It is to be noted that the implementations of the first through-slots 231 according to this Embodiment are also applicable to Embodiment 1. For example, each of the first through-slots 231 in Embodiment 1 may also be provided with second through-slots 240 at their circumferentially opposing ends. Moreover, in general, the elastic tube 310 is structurally similar to the elastic tube 210, and the elements of the elastic tube 210 and the elastic tube 310 indicated at the same reference numerals (e.g., the strain gauges 220) are usually similar in terms of construction and operation.

Embodiment 3

Figure 8:
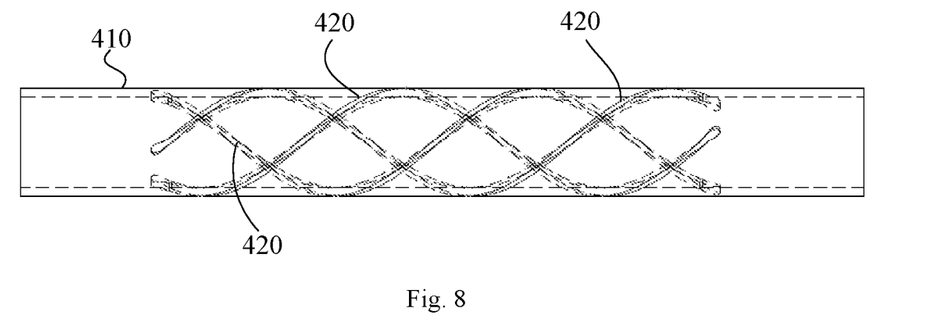
FIG. 8 is a structural schematic of an elastic tube with spiral through-slots according to Embodiment 3 of the present invention.
Figure 9:
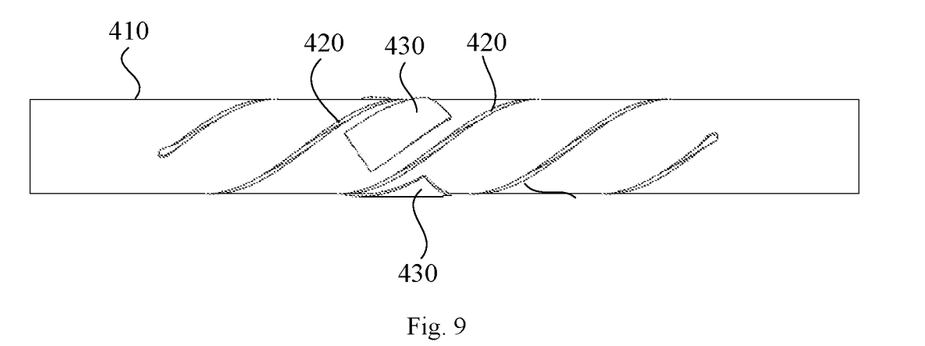
FIG. 9 schematically illustrates how strain gauges are distributed on the elastic tube according to Embodiment 3 of the present invention.

FIG. 8 is a structural schematic of an elastic tube with spiral through-slots according to Embodiment 3 of the present invention, and FIG. 9 schematically illustrates how strain gauges are distributed on the elastic tube according to Embodiment 3 of the present invention.

As shown in FIGS. 8 to 9, there is/are spiral third through-slot(s) 420 cut in the outer surface of the elastic tube 410. The number of the spiral through-slot(s) may be one, two or more than two. The greater the number of the third through-slot(s) 420 is, the higher the circumferential uniformity of the elastic tube 410 and the lower the elastic modulus thereof will be. In practice, the number of the spiral through-slot(s) may be properly selected according to a strain measurement range of the strain gauges 430. Preferably, when three strain gauges 430 are used, three third through-slots 420 are formed, so that each of the strain gauges 430 is disposed between corresponding two of the third through-slots 420.

In case of two or more such spiral through-slot(s), they are spaced apart at a pitch of 1.0-6.0 mm and extend 1 to 3 turns, preferably 2 turns. Moreover, each of them has a width of 0.05-0.2 mm. Further, in order to prevent stress concentration, both ends of each of the third through-slots 420 are curved, for example, semi-oval.

With continued reference to FIG. 9, the strain gauges 430 are attached consistently with the direction of the spirals and are arranged at an angle to the axis of the elastic tube 410. That is, the strain gauges 430 extend in the same direction as the spirals. Preferably, the strain gauges 430 are disposed in central portions of the spirals. Similarly, the strain gauges 430 are circumferentially distributed evenly with respect to the elastic tube 410. In this Embodiment, centers of the three strain gauges 430 equally trisect the circumference of the elastic tube 410 into identical 120-degree arcs.

Embodiment 4

Figure 10:
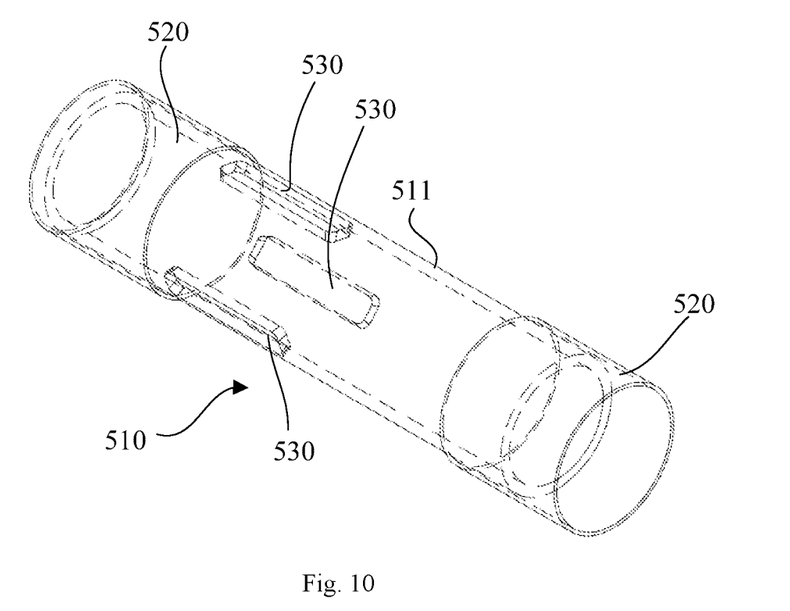
FIG. 10 is a structural schematic of an elastic tube with axial through-slots according to Embodiment 4 of the present invention.
Figure 11:
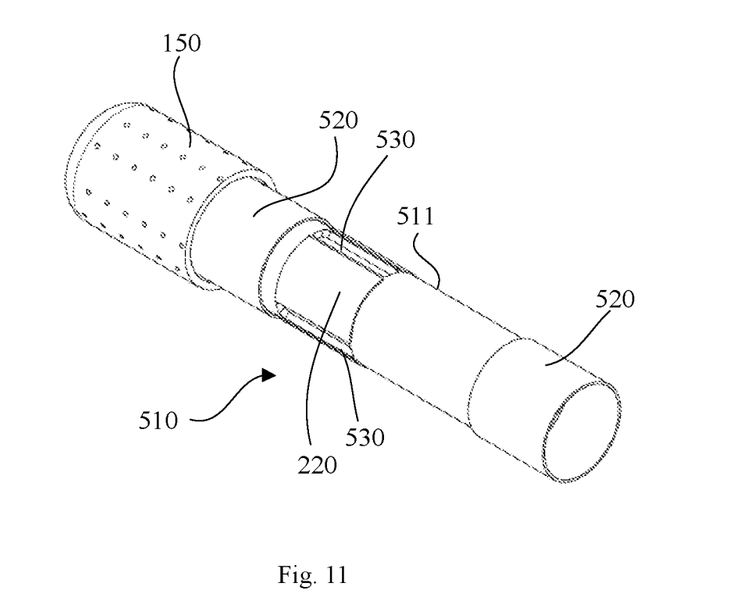
FIG. 11 is a structural schematic of a distal portion of an ablation catheter according to Embodiment 4 of the present invention.

FIG. 10 is a structural schematic of an elastic tube with axial through-slots according to Embodiment 4 of the present invention, and FIG. 11 is a structural schematic of a distal portion of an ablation catheter according to Embodiment 4 of the present invention.

As shown in FIGS. 10 to 11, in this Embodiment, the elastic tube 510 includes a tubular body 511 and sleeves 520 for receiving opposing end portions of the tubular body 511, making the whole structure of the elastic tube 510 thinner in the middle and thicker at the ends, appearing in cross section like the letter "I". When a distal end of the elastic tube 510 is stressed, the tubular body 511 can easily sense a resulting strain, improving the elasticity of the elastic tube 510.

The sleeves 520 may be either a nickel titanium alloy or a stainless steel, and the sleeves 520 are attached to the tubular body 511 by means of laser welding or an adhesive. A diameter ratio of the sleeves 520 to the tubular body 511 ranges from 1.1 to 2.0, with 1.2 being preferred. One of the sleeves 520 is further glued or laser-welded to the ablation electrode 150.

In particular, for example, three or more fourth through-slots 530 are cut in the tubular body 511 in such a manner that they are circumferentially distributed evenly with respect to the elastic tube 210. The fourth through-slots 530 may be obround, oval or round slots, or chamfered rectangles, or of another shape in order to impart higher elasticity of the elastic tube 510 and low strength to the elastic tube 510 while preventing stress concentration. In case of oblong fourth through-slots 530, each of them has an axial length of 2.0-5.0 mm and a circumferential width of 0.05-0.3 mm.

In the case shown in FIG. 10, the fourth through-slots 530 are spaced apart from one another circumferentially with respect to the tubular body 511, a strain gauge 220 is disposed between every adjacent two of the fourth through-slots 530. With this design, when the distal end of the elastic tube 510 is stressed, the strain gauges 220 arranged among the fourth through-slots 530 can sense a resulting tensile or compressive strain of the solid part.

While a number of preferred embodiments of the present invention have been described above, the scope thereof is not limited to these disclosed embodiments. For example, multiple strain gauges may be arranged side-by-side between every adjacent two of the fourth through-slots. As another embodiment, one or more fourth through-slot sets, each containing a plurality of fourth through-slots, may be formed, with one or more strain gauges being disposed between every adjacent two of the fourth through-slot sets. As still another embodiment, between every adjacent two of the third through-slots, may be disposed a plurality of strain gauges each extending in the same direction as the spiral through-slots.

While the electrophysiology catheter according to the present invention is described in detail with them being implemented as an ablation catheter for the purpose of illustration, the present invention is not limited thereto, because the electrophysiology catheter may also be, for example, a mapping catheter or the like.

Figure 12:
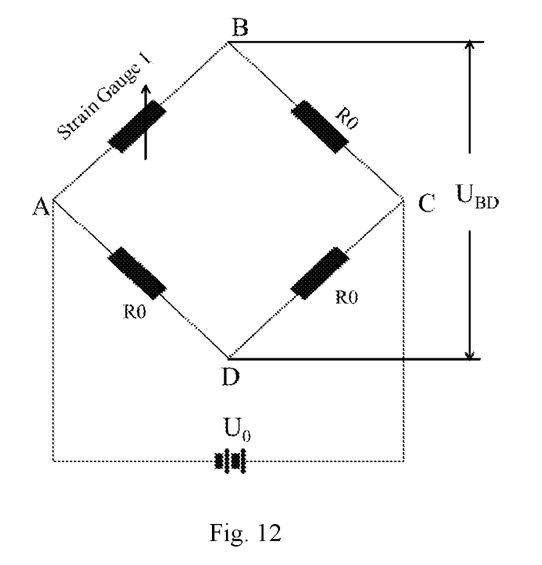
FIG. 12 is a diagram schematically showing a Wheatstone bridge circuit of a single strain gauge in one of the foregoing Embodiments of the present invention.
Figure 13:
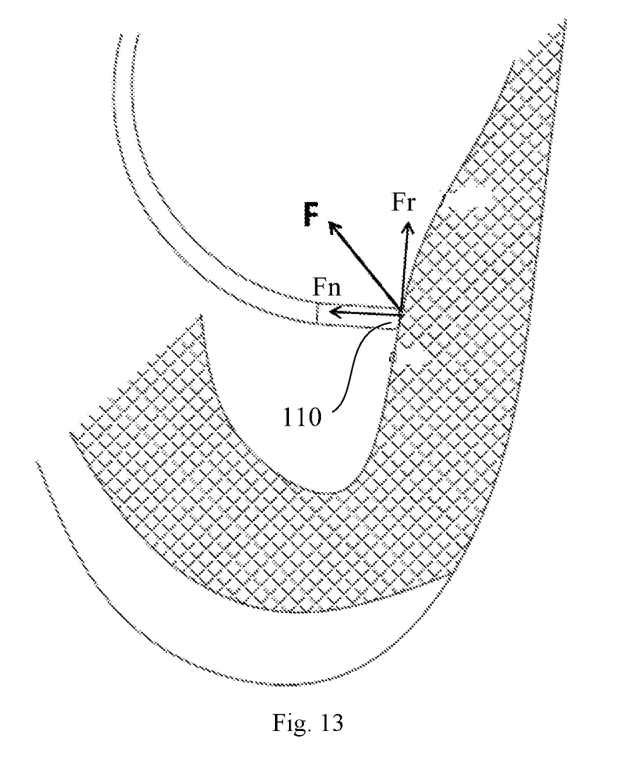
FIG. 13 schematically illustrates a force generated upon a distal portion according to one of the foregoing Embodiments coming into contact with a tissue.
Figure 14:
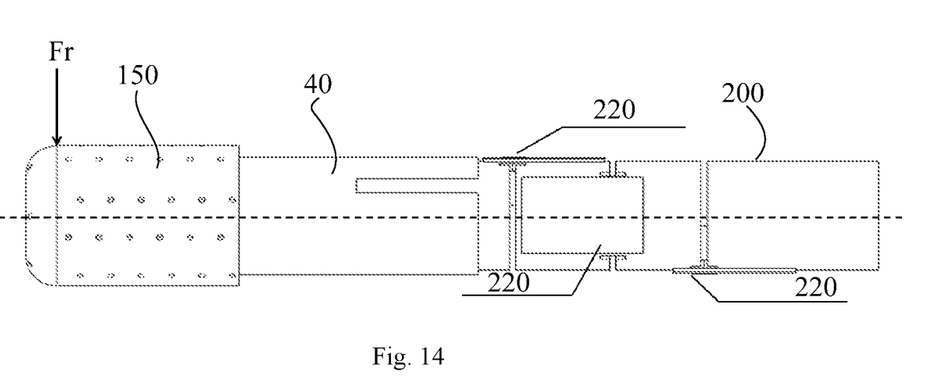
FIG. 14 schematically illustrates a force sensor according to one of the foregoing Embodiments, which is laterally stressed.

FIG. 12 is a schematic circuit diagram of the Wheatstone bridge of one of the strain gauges as detailed above in conjunction with the foregoing Embodiments. FIG. 13 schematically illustrates a force generated upon a distal portion according to one of the foregoing Embodiments coming into contact with a tissue. FIG. 14 schematically illustrates a force sensor according to one of the foregoing Embodiments, which is laterally stressed. Hereinafter, although the force sensor subject to the lateral force Fr, as shown in FIG. 14, will be described as being implemented as the force sensor 200 of Embodiment 2 for the purpose of exemplification, those skilled in the art will readily appreciate that the following description is also applicable to the force sensors of the other Embodiments.

Referring to FIG. 13, for example, when the catheter distal portion 110 comes into contact with the myocardium, the elastic tube 210 (for the purpose of illustration and the same applies to the following) will be deformed and the strain gauge 220 will be accordingly stretched or compressed. Specifically, when the strain gauge 220 is stretched, the metal wire pattern of the strain-sensitive grid therein will become longer, leading to an increase in its resistance. When the strain gauge 220 is compressed, the metal wire pattern will become shorter, leading to a decrease in the resistance. That is, irrespective of stretching or compression, the resistance will vary. The change in the resistance of the strain gauge 220 is then amplified, for example, by the Wheatstone bridge of FIG. 12, and output as a voltage variation. The Wheatstone bridge may either be implemented as a single-bridge or selected as a half- or full-bridge in order to facilitate signal amplification.

Referring to FIGS. 13 and 14, the contact force F experienced by the catheter distal portion 110 may be decomposed into the lateral component Fr and an axial component Fn. Referring to FIG. 13, based on the pure-bending theory, under the action of the lateral component Fr, the strain gauge 220 will be stretched to give a positive strain value if it is located above the central axis of the ablation catheter 100, or compressed to give a negative strain value if it is located under the central axis of the ablation catheter 100, or almost remain the same to give a zero strain value if it is located on the central axis. In this way, strain sensing in three directions is accomplishable by three strain gauges 220, and their resistance changes corresponding to lateral and axial strains can be measured and then processed by the microprocessors 190 to determine the contact force F and an associated contact angle.

In those Embodiments, the strain gauges 220 are connected to respective microprocessor systems each including a corresponding one of the data acquisition device 180. The data acquisition device 180 is configured for collecting electrical signals from the respective strain gauge 220 and providing the collected electrical signals to the microprocessor 190. The microprocessor 190 is configured for computational processing of the electrical signals from all the strain gauges 220.

Each of the microprocessor systems may further include at least one measuring device that is wired to the data acquisition device 180 and to the microprocessor 190 and is capable of direct resistance measurement or indirect voltage or current measurement. Each of the microprocessor systems may be powered at 1.0-10 V, preferably 1.25 V.

In summary, compared to the design with the strain gauges overlapping the hollow portion, arranging them over solid portions of the elastic tube in the electrophysiology catheter of the present invention allows the strain gauges to collect more accurate electrical signals and thus improve contact force measurement accuracy of the catheter distal portion.

In particular, disposing the strain gauges between opposing ends of the arcuate first through-slots or between adjacent spiral third through-slots or between adjacent axially-extending fourth through-slots in accordance with the present invention enable the strain gauges to collect higher-quality electrical signals. Moreover, the spiral third through-slots impart higher circumferential uniformity to the elastic tube, helping in collecting more accurate electrical signals.

In more particular, the axially-extending second through-slots provided at the ends of the first through-slots in accordance with the present invention can further lower the rigidity of the elastic tube, thereby increasing the deformability of the elastic tube, helping in enhancing the electrical signals collected by the strain gauges and making the measurement results more accurate.

Further, the force sensor according to the present invention is less bulky, more sensitive, less affected by magnetic fields, immune from temperature variations and cost-effective. Furthermore, in addition to the magnitude of a contact force exerted by the surface of a vessel wall or organ on the catheter distal portion, the plurality of strain gauges can also measure axial and lateral components of the force and an associated contact angle as well. This can provide the physician with valuable additional information based on which better surgical outcomes can be obtained.

The description presented above is merely that of a few preferred embodiments of the present invention and does not limit the scope thereof in any sense. Any and all changes and modifications made by those of ordinary skill in the art based on the above teachings fall within the scope as defined in the appended claims.

The invention claimed is:

1. A force sensor, comprising an elastic tube and at least one strain gauge, the elastic tube having a hollow portion formed in a wall thereof, the strain gauge having no overlap with the hollow portion,
   wherein the hollow portion comprises at least one arcuate first through-slot, each first through-slot has opposing ends between which one strain gauge is arranged or a plurality of strain gauges are arranged side-by-side.

2. The force sensor of claim 1, wherein the hollow portion comprises a plurality of first through-slots axially spaced apart from one another on the elastic tube and staggered from one another along a circumferential direction of the elastic tube.

3. The force sensor of claim 2, wherein there are more than one strain gauges, the hollow portion comprises two first through-slots, wherein one of the strain gauges is disposed between the opposing ends of one of the first through-slots, while two strain gauges of the strain gauges are disposed side-by-side between the opposing ends of an other one of the first through-slots, and wherein the one of the first through-slots has a length greater than a length of the other one of the first through-slots.

4. The force sensor of claim 2, wherein there are more than one strain gauges, the hollow portion comprises more than two first through-slots distributed evenly along the circumferential direction of the elastic tube, each first through-slot has two opposing ends between which at least one strain gauge of the strain gauges is disposed.

5. The force sensor of claim 2, wherein a central axis of the strain gauge along an axial direction of the elastic tube is parallel to a central axis of the elastic tube.

6. The force sensor of claim 1, wherein the hollow portion comprises at least one through-slot set, each through-slot set containing a plurality of first through-slots aligned with one another axially and having two opposing ends between which one strain gauge is arranged or a plurality of strain gauges are arranged side-by-side.

7. The force sensor of claim 6, wherein a length of the strain gauge in an axial direction of the elastic tube is greater than or equal to a width of the through-slot set in the axial direction of the elastic tube.

8. The force sensor of claim 6, wherein the hollow portion comprises a plurality of through-slot sets axially spaced apart from one another on the elastic tube and staggered from one another along a circumferential direction of the elastic tube.

9. The force sensor of claim 8, wherein there are more than one strain gauges, the hollow portion comprises two through-slot sets, wherein one of the strain gauges is disposed between opposing ends of one of the through-slot sets, while two strain gauges of the strain gauges are disposed side-by-side between the opposing ends of an other one of the through-slot sets, and wherein the one of the through-slot sets has a length greater than a length of the other one of the through-slot sets.

10. The force sensor of claim 8, wherein there are more than one strain gauges, the hollow portion comprises more than two through-slot sets distributed evenly along the circumferential direction of the elastic tube, each through-slot set having two opposing ends between which at least one of the strain gauges is disposed.

11. The force sensor of claim 8, wherein a central axis of the strain gauge along an axial direction of the elastic tube is parallel to a central axis of the elastic tube.

12. The force sensor of claim 1, wherein each of the first through-slots is provided at the opposing ends thereof with second through-slots extending along an axial direction of the elastic tube.

13. The force sensor of claim 12, wherein the second through-slot has an obround, oval or round shape.

14. An electrophysiology catheter, comprising a catheter distal portion, wherein the catheter distal portion is provided with a force sensor of claim 1.

15. The electrophysiology catheter of claim 14, wherein the elastic tube is provided with sleeves at opposing ends thereof and forms an "I"-shaped structure.

16. A force sensor, comprising an elastic tube and at least one strain gauge, the elastic tube having a hollow portion formed in a wall thereof, the strain gauge having no overlap with the hollow portion, wherein the hollow portion comprises at least one spiral third through-slot, and wherein the strain gauge extends in a same direction as the spiral third through-slot.

17. The force sensor of claim 16, wherein the hollow portion comprises a plurality of the third through-slots spaced apart from one another, one or more strain gauges are disposed between every adjacent two of the plurality of the third through-slots.

18. The force sensor of claim 16, wherein the at least one strain gauge is disposed in central portions of the third through-slot.

19. The force sensor of claim 16, wherein the third through-slot is formed by spiral cutting at a pitch of 1.0-6.0 mm and a number of turns of 1-3, the third through-slot has a width of 0.05-0.2 mm.

* * * * *